US005507739A

United States Patent [19]
Vassiliadis et al.

[11] Patent Number: 5,507,739
[45] Date of Patent: Apr. 16, 1996

[54] DENTAL LASER

[75] Inventors: Arthur Vassiliadis, Mountain View; David R. Hennings, Newcastle; Joseph W. Schaffer, Mountain View; David J. Fullmer, Foster City; Michael H. Brewer, Felton, all of Calif.; Terry D. Myers, Bloomfield Hills; William D. Myers, Birmingham, both of Mich.

[73] Assignee: American Dental Technologies, Inc., Southfield, Mich.

[21] Appl. No.: 898,730

[22] Filed: Jun. 15, 1992

(Under 37 CFR 1.47)

[51] Int. Cl.$^6$ ..................................................... A61B 17/36
[52] U.S. Cl. ........................ 606/3; 606/2; 607/89; 372/23
[58] Field of Search ............................ 606/2, 3, 10–19; 607/89; 372/21–23

[56]  References Cited

U.S. PATENT DOCUMENTS

| | | | |
|---|---|---|---|
| 4,757,507 | 6/1988 | Wondrazek | 372/23 |
| 4,791,927 | 12/1988 | Menger | 606/3 |
| 4,940,411 | 7/1990 | Vassiliadis et al. | 606/3 |
| 5,009,658 | 4/1991 | Damgaard-Iversen et al. | 606/3 |
| 5,066,291 | 11/1991 | Stewart | 606/3 |
| 5,125,922 | 6/1992 | Dwyer | 606/2 |

Primary Examiner—Stephen C. Pellegrino
Assistant Examiner—M. Peffley
Attorney, Agent, or Firm—Gifford, Krass, Groh, Sprinkle, Patmore, Anderson & Citkowski

[57]  ABSTRACT

A dual wavelength laser is disclosed for use in dental therapeutic applications. The dual wavelength laser includes a laser cavity in which a laser crystal is disposed and preferably the laser crystal is an Nd:YAG laser, which, upon excitation, lases at two different wavelengths, each of which has a different gain. A shutter, or alternatively an optical filter, is selectively disposed within the optical path of the laser crystal whereupon the higher gain wavelength is selectively suppressed. Thus, with the shutter or optical filter removed from the optical path, the laser lases at its higher gain wavelength. Conversely, with the shutter or filter positioned within the optical path, the higher gain wavelength is effectively suppressed so that the laser crystal lases at the lower gain wavelength.

6 Claims, 1 Drawing Sheet 5,507,739

DENTAL LASER

BACKGROUND OF THE INVENTION

1. Field of the Invention

The present invention relates generally to lasers and, more particularly, to a dual wavelength laser for use in dental therapeutic applications.

2. Description of the Prior Art

There are a number of previously known lasers that are used in dental applications. One such laser is a neodymium doped yttrium aluminum garnet laser (Nd:YAG) which, when excited, produces a pulsed output used for dental therapeutic applications. These dental therapeutic applications include, for example, the cutting and eradication of soft tissue, desensitization of teeth, endontic procedures and other dental procedures.

For an Nd:YAG laser crystal, as well as other laser crystals, the wavelength of the emission is a function of the stimulated emission section and thus the gain of the laser crystal. For an Nd:YAG laser, the highest gain wavelength is 1.06 microns so that, upon excitation, the Nd:YAG laser crystal will normally lase at its highest gain wavelength and thus at 1.06 microns.

The Nd:YAG laser, however, when excited, can also lase at different wavelengths, such as 1.32, 0.96 and 1.44 microns. All of these other wavelengths, however, have a higher lasing threshold, and thus lower gain, than the 1.06 wavelength so that normally the Nd:YAG laser, once excited, lases at its maximum gain wavelength, i.e. 1.06 microns.

For many dental therapeutic applications, the 1.06 micron wavelength of the Nd:YAG laser has proven superior to the other, lower gain wavelengths of the Nd:YAG laser. In other applications, especially the cutting of soft tissue, however, the Nd:YAG laser operated at 1.32 microns has proven superior to the 1.06 microns wavelength due to the higher water absorption at 1.32 microns versus 1.06 microns.

Consequently, it would be desirable to have two lasers in the dental office, i.e. one laser which lases at 1.06 microns and a second laser which lases at 1.32 microns. Such a situation, however, is very costly due to the high cost of each laser.

SUMMARY OF THE PRESENT INVENTION

The present invention overcomes the above mentioned disadvantages of the previously known dental lasers by providing a single laser which can be selectively excited to lase at either 1.06 or 1.32 microns.

In brief, the dental therapeutic laser of the present invention comprises a laser cavity in which an elongated laser crystal is disposed. Preferably, the laser crystal is a neodymium doped yttrium aluminum garnet crystal (Nd:YAG).

Conventional means, such as a flash lamp, are then used to excite the crystal so that the crystal lases at two wavelengths. Means are then provided for selectively suppressing the higher gain 1.06 microns wavelength so that the laser continues to lase at its next lower gain wavelength of 1.32 microns.

In one form of the invention, a three mirror resonator with a shutter assembly is employed to selectively obtain laser operation at either 1.06 or 1.32 microns. In the three mirror resonator, one mirror is positioned in alignment with one end of the laser crystal which reflects between 10% and 98% of the laser emission at both 1.06 and 1.32 microns.

A pair of axially spaced mirrors are then positioned adjacent the opposite end of the laser rod. The first mirror, i.e. the mirror closest to the laser rod is coated with a material which produces high reflection of laser emission at 1.32 microns and, simultaneously, is highly transmissive at 1.06 microns. Thus, laser emission at 1.32 microns is normally reflected by the first mirror back toward the laser rod while the laser emission at 1.06 microns passes through the first mirror.

The second mirror is highly reflective of laser emissions at 1.06 microns. In addition, an optical shutter is selectively disposed between the two mirrors.

With the shutter positioned in between the mirrors, the shutter effectively suppresses the laser emission at the higher gain 1.06 wavelength whereupon laser operation at 1.32 microns will continue. Conversely, with the shutter removed from the optical path, the 1.06 microns wavelength laser emission will be effectively reflected by the second mirror so that, due to the higher gain of the 1.06 wavelength, laser emission will continue at the 1.06 wavelength.

In a second embodiment of the invention, a partial reflector is positioned in the optical path adjacent one end of the laser rod while a single mirror is positioned in the optical path at the opposite end of the laser rod. This single mirror, furthermore, is highly reflective of laser emission at both 1.06 microns and 1.32 microns.

An optical filter is then selectively disposed in the optical path between the end of the laser rod and the mirror. This optical filter includes a coating which is highly absorbent of laser emission at 1.06 microns and, conversely, highly transmissive of laser emission at 1.32 microns. Thus, with the optical filter removed from the optical path, laser emission proceeds at the dominant or higher gain 1.06 microns wavelength. Conversely, with the optical filter positioned within the optical path, the higher gain 1.06 microns wavelength laser emission is effectively suppressed while simultaneously permitting resonance at the lower gain 1.32 microns wavelength.

Any conventional means, such as a solenoid assembly, can be used to selectively position either the shutter or the filter within the optical path.

BRIEF DESCRIPTION OF THE DRAWING

A better understanding of the present invention will be had upon reference to the following detailed description, when read in conjunction with the accompanying drawings, wherein like reference characters refer to like parts throughout the several views, and in which.

DETAILED DESCRIPTION OF PREFERRED EMBODIMENTS OF THE PRESENT INVENTION

Figure 1:
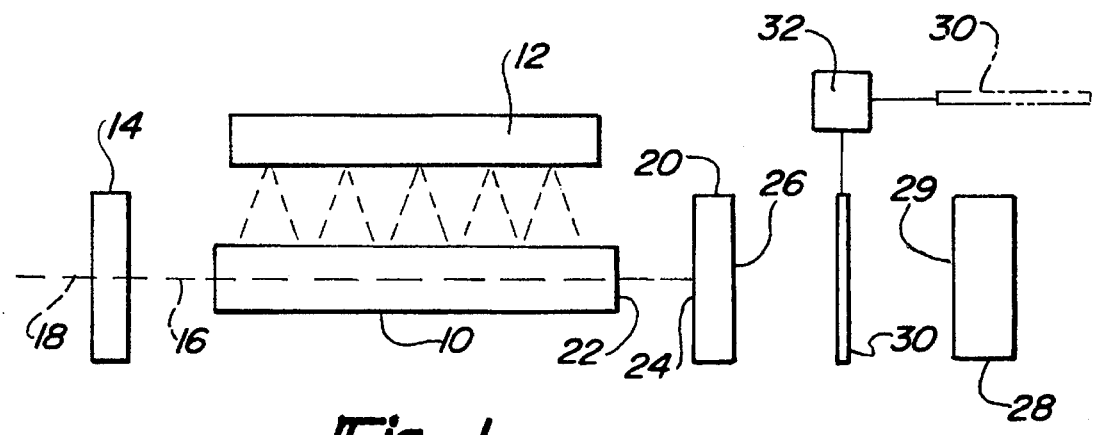
FIG. 1 is a longitudinal partial diagrammatic view illustrating a first preferred embodiment of the present invention and illustrating the laser operation at a lower gain wavelength.

With reference first to FIG. 1, a first preferred embodiment of the present invention is thereshown and comprises an elongated laser rod or crystal 10 disposed in a laser cavity.

A conventional flash lamp 12 is used to excite or stimulate the laser rod 10 into laser emission.

The laser rod 10 is preferably a neodymium doped yttrium aluminum garnet (Nd:YAG) laser which, when excited, lases at a number of different wavelengths, namely 0.96, 1.06, 1.32 and 1.44 microns. However, of all these wavelengths, the stimulated emission cross section, and thus the gain, of the 1.06 wavelength is many times greater than the emission cross section at the other wavelengths. Similarly, laser emission at 1.32 microns enjoys the second highest stimulated emission cross section and thus the second highest gain after the 1.06 microns wavelength.

A partial reflector 14 is positioned within the optical path 16 of the laser rod 10. This partial reflector 14 reflects between 10% and 98% of the laser emission from the rod 10 at both 1.06 and 1.32 microns. Consequently, a portion of the laser emission impinging upon the partial reflector 14 passes through the reflector 14, as shown at 18, and forms the laser emission from the laser cavity.

Still referring to FIG. 1, a first mirror 20 is positioned within the optical path 16 of the laser rod 10 adjacent the opposite end 22 of the rod 10. A coating is provided on one side 24 of the mirror 20 which is highly reflective at 1.32 microns and preferably has a reflectance of about 99.5% at 1.32 microns. Simultaneously, the coating on the side 24 of the mirror 20 is highly transmissive to laser radiation at 1.06 microns and preferably transmits more than 95% of laser emission at 1.06 microns. The opposite side 26 of the mirror 20 is also highly transmissive of laser radiation at 1.06 microns.

A second mirror 28 is also positioned within the optical path 16 of the laser rod 10 at a position spaced outwardly from the mirror 20. One side 29 of the mirror 28 is highly reflective of laser radiation at 1.06 microns as well as other wavelengths.

Still referring to FIG. 1, an optical shutter 30 is selectively moved between a position within the optical path 16, as shown in solid line, and to a position outside of the optical path 16, as shown in phantom line, by a solenoid assembly 32. This optical shutter 30 is constructed of a material which is highly absorbent, and thus non-reflective and non-transmissive of laser emission. Preferably, the shutter 30 is constructed of an opaque material, such as aluminum.

The operation of the FIG. 1 embodiment will now be described. With the shutter 30 positioned in the optical path as shown in solid line in FIG. 1, the laser rod 10 is excited by the flash lamp 12. Once excited, the laser rod 10 emits laser radiation at a number of different frequencies, including 1.06 microns and 1.32 microns. The partial reflector 14 and first mirror 20 form a resonator for the laser at 1.32 microns due to the high reflectivity of the mirror 20 at 1.32 microns. Simultaneously, the laser emission at the higher gain wavelength of 1.06 microns passes through the first mirror and is absorbed by the opaque shutter 30. Since the higher gain 1.06 micron laser emission is suppressed by the shutter 30, laser emission at 1.32 microns wavelength is emitted from the laser cavity as shown at 18.

Conversely, with the shutter 30 moved to the position shown in phantom line, the second mirror 28 and partial reflector form a resonator for the higher gain laser emission at 1.06 microns. Since the gain of the laser emission at 1.06 microns is many fold the gain of the emission at 1.32 microns, the laser emission will continue at 1.06 microns along the optical path 18 from the laser cavity.

Figure 2:
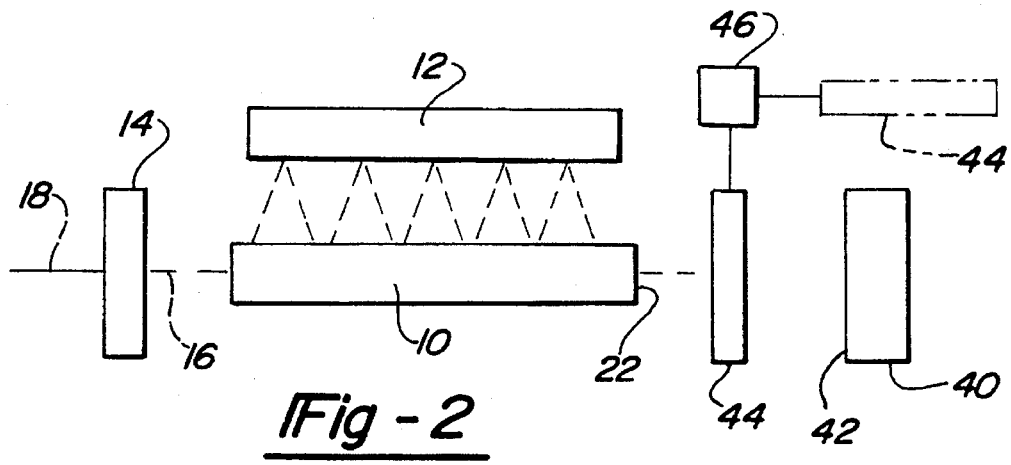
FIG. 2 is a longitudinal sectional view similar to FIG. 1, but showing a second preferred embodiment of the present invention.

With reference now to FIG. 2, a second embodiment of the present invention is thereshown. In the second embodiment, a flash lamp or other excitation means 12 is used to excite the laser rod 10 which, as before, is an Nd:YAG laser crystal. The partial reflector 14 is also positioned in the optical path 16 adjacent one end of the laser rod 10.

Unlike the FIG. 1 embodiment, however, a single mirror 40 is provided in the optical path 16 of the laser rod 10 adjacent its end 22. This mirror 40 includes a surface 42 which is highly reflective at both 1.06 microns and 1.32 microns.

An optical filter 44 is selectively moved by a solenoid mechanism 46, or other electromechanical means, between a position shown in solid line in which the filter 44 is positioned within the optical path 16 between the end 22 of the laser rod 10 and the mirror 40, and a position shown in phantom line in which the optical filter 44 is removed from the optical path 16. The filter 44 is constructed of a material which has high absorption of laser emission at 1.06 microns but which is also highly transmissive of laser emission at 1.32 microns.

Preferably, the optical filter 44 is constructed of a thin material, such as yttrium iron garnet, and is anti-reflection coated on both of its sides for both wavelengths 1.06 microns and 1.32 microns In operation, with the filter 44 positioned within the optical path 16 (solid line in FIG. 2) the optical filter 44 effectively absorbs and thus suppresses the higher gain laser emission at 1.06 microns. Simultaneously, the reflector 14 and mirror 40 form a resonator for the lower gain laser emission at 1.32 microns Conversely, with the filter 44 moved to its second position removed from the optical path 16 (phantom line in FIG. 2) the mirror 40 and partial reflector 14 form a resonator for the laser emission at the higher gain 1.06 microns wavelength.

Alternatively, a thin dichroic mirror which reflects at 1.06, but transmits at 1.32 microns can replace the filter 44.

From the foregoing, it can be seen that the present invention provides a simple and yet highly effective laser assembly for dental uses in which a single laser rod can be selectively excited to lase at either 1.06 microns or 1.32 microns wavelengths. This thus allows greater flexibility in selection of the appropriate wavelengths for the desired dental therapeutic application.

The present invention can also be used to obtain dual or even multiple wavelength laser operation for lasers other than Nd:YAG lasers. For example, a holmium doped YAG laser lases at both 2.1 microns and 3.9 microns. Selective suppression of either wavelength will allow operation of the other wavelength.

Similarly, an erbium doped YAG laser lases at 1.65 microns, 2.3 microns and 2.9 microns. By selectively suppressing two of the wavelengths, laser operation continues at the third wavelength.

Having described our invention, however, many modifications thereto will become apparent to those skilled in the art to which it pertains without deviation from the spirit of the invention as defined by the scope of the appended claims.

We claim:

1. A laser for use in dental therapeutic applications comprising:

a laser cavity, a laser crystal, said crystal being disposed in said cavity and capable of lasing at two different wavelengths, means for exciting said crystal so that said crystal lases at said two wavelengths, means for selectively suppressing one of said wavelengths so that said crystal continues to lase at the other of two wavelengths wherein said laser crystal is elongated and emits laser radiation out each end, a partial reflector positioned in alignment with one end of said crystal and wherein said suppressing means comprises a first and second mirror being positioned in alignment with the other end of said laser crystal, said first mirror being spaced from said second end of said crystal by a distance which is resonant with said first wavelength, said second mirror being spaced from said second end of said crystal by a distance which is resonant with said second wavelength, said first mirror being substantially transparent to said second wavelength, an optically opaque shutter and means for selectively positioning said shutter between said first and second mirrors.

2. The invention as defined in claim 1 wherein said laser crystal comprises a neodymium doped yttrium aluminum garnet crystal.

3. The invention as defined in claim 2 wherein one wavelength comprises 1.06 microns and the other wavelength comprises 1.32 microns.

4. The invention as defined in claim 1 and comprising a coating on said first mirror which is highly reflective at said first wavelength and highly transmissive at said second wavelength.

5. The invention as defined in claim 1 and comprising a coating on said reflector which is partially reflective at both wavelengths.

6. The invention as defined in claim 1 wherein said positioning means comprises a solenoid.

* * * * *

UNITED STATES PATENT AND TRADEMARK OFFICE
CERTIFICATE OF CORRECTION

PATENT NO. : 5,507,739
DATED : April 16, 1996
INVENTOR(S) : Vassiliadis et al.

It is certified that error appears in the above-indentified patent and that said Letters Patent is hereby corrected as shown below:

Column 1, line 21, after "emission", insert --cross--

Signed and Sealed this

Seventeenth Day of September, 1996

Attest:

BRUCE LEHMAN

Attesting Officer          Commissioner of Patents and Trademarks